United States Patent
Cotte et al.

(10) Patent No.: US 7,192,868 B2
(45) Date of Patent: Mar. 20, 2007

(54) METHOD OF OBTAINING RELEASE-STANDING MICRO STRUCTURES AND DEVICES BY SELECTIVE ETCH REMOVAL OF PROTECTIVE AND SACRIFICIAL LAYER USING THE SAME

(75) Inventors: John Michael Cotte, New Fairfield, CT (US); Nils Deneke Hoivik, Pleasantville, NY (US); Christopher Vincent Jahnes, Upper Saddle River, NJ (US)

(73) Assignee: International Business Machines Corporation, Armonk, NY (US)

( * ) Notice: Subject to any disclaimer, the term of this patent is extended or adjusted under 35 U.S.C. 154(b) by 60 days.

(21) Appl. No.: 11/053,610

(22) Filed: Feb. 8, 2005

(65) Prior Publication Data

US 2006/0178004 A1 Aug. 10, 2006

(51) Int. Cl.
*H01L 21/302* (2006.01)
*H01L 21/461* (2006.01)

(52) U.S. Cl. ............... 438/689; 438/311; 438/680; 438/692; 438/933; 257/E21; 257/17; 257/168; 257/182

(58) Field of Classification Search ........... 438/689, 438/311, 700, 736, 706, 712, 513, 680, 692, 438/679, 752, 753, 931, 933, 954
See application file for complete search history.

(56) References Cited

U.S. PATENT DOCUMENTS

| | | | |
|---|---|---|---|
| 6,232,150 B1 * | 5/2001 | Lin et al. ................. | 438/119 |
| 6,362,109 B1 * | 3/2002 | Kim et al. ................. | 438/706 |
| 6,436,853 B2 * | 8/2002 | Lin et al. ................. | 438/800 |
| 6,458,618 B1 * | 10/2002 | Allen et al. ............... | 438/53 |
| 6,666,979 B2 | 12/2003 | Chinn et al. .............. | 438/745 |
| 6,736,987 B1 * | 5/2004 | Cho, II .................... | 216/58 |
| 6,797,189 B2 * | 9/2004 | Hung et al. ............... | 216/67 |
| 6,806,205 B2 | 10/2004 | Jang et al. ................ | 438/745 |

OTHER PUBLICATIONS

Herman, et al., "MEMS Test Structures for Mechanical Characterization of VLSI Thin Films" Proc. SEM Conference. Portland Oregon, Jun. 4-6, 2001.
Micro Electro Mechanical Systems (MEMS), http://mems.nist.gov/home.html, Contact: Michael Gaitan, Project Leader (mems@nist.gov) last printed Dec. 23, 2004.

* cited by examiner

*Primary Examiner*—David Nhu
(74) *Attorney, Agent, or Firm*—Scully, Scott, Murphy & Presser, P.C.; Robert M. Trepp, Esq.

(57) ABSTRACT

A method of patterning and releasing chemically sensitive low k films without the complication of a permanent hardmask stack, yielding an unaltered free-standing structure is provided. The method includes providing a structure including a Si-containing substrate having in-laid etch stop layers located therein; forming a chemically sensitive low k film and a protective hardmask having a pattern atop the structure; transferring the pattern to the chemically sensitive low k film to provide an opening that exposes a portion of the Si-containing substrate; and etching the exposed portion of the Si-containing substrate through the opening to provide a cavity in the Si-containing substrate in which a free-standing low k film structure is formed, while removing the hardmask. In accordance with the present invention, the etching comprises a $XeF_2$ etch gas.

26 Claims, 7 Drawing Sheets

METHOD OF OBTAINING RELEASE-STANDING MICRO STRUCTURES AND DEVICES BY SELECTIVE ETCH REMOVAL OF PROTECTIVE AND SACRIFICIAL LAYER USING THE SAME

FIELD OF THE INVENTION

The present invention relates to semiconductor device fabrication, and more particularly to a method of fabricating a semiconductor structure that includes a free-standing micro structure (or layer). The method of the present invention includes a selective etch process that is capable of removing a protective layer and a sacrificial layer.

BACKGROUND OF THE INVENTION

Evaluation of mechanical properties of thin films used in semiconductor processing such as, for example, residual stress, CTE (coefficient of thermal expansion) and Young's modulus, is critical for the understanding of the performance (both mechanical and electrical) of the materials used. As the mechanical properties can significantly vary from wafer to wafer, and with process conditions, obtaining a clear understanding of the effects of processing is very valuable to understanding yield and performance. Currently, the processes in which these films are tested and characterized are quite rudimentary and labor intensive.

By creating free-standing film structures, which are released from the substrate to form suspended devices such as cantilever and bridges, using micro-machining techniques, and or processing, the mechanical properties of the film can be accurately determined. This approach has been extensively researched in the semiconductor industry, and as an example, NIST (National Institute of Standards and Technology) has developed three standards for the determination of intrinsic stress and characterization of elastic properties in very large scale integration (VLSI) thins films. This is reported, for example, in D. Herman, M. Gaitan, D. Devoe, "MEMS Test Structures for Mechanical Characterization of VLSI Thin Films", Proc. SEM Conference, Portland, Oreg., Jun. 4–6, 2001. See also http://mems.nist.gov/.

However, procedures described above have been developed for conventional films used in VLSI/CMOS (complementary metal oxide semiconductor) technology whereas low k dielectric films (having a dielectric constant of less than silicon dioxide, $SiO_2$) are very sensitive to most common chemicals and gases used in standard micro-machining processes. Subsequently, the low k films will not typically survive the general micro-machining sacrificial etch and release techniques widely used. See, for example, U.S. Pat. No. 6,808,205 to Jang, et al. and U.S. Pat. No. 6,666,979 to Chinn, et al, which describe typical micro-machining sacrificial etch and release techniques.

In view of the above, there is a need for providing a method for the micro-machining of low k films, which minimizes the problems of patterning and releasing chemically sensitive low k films, without the complication of a permanent hardmask stack. Moreover, there is a need for providing a method that yields unaltered free-standing structures.

SUMMARY OF THE INVENTION

The present invention provides a method of patterning and releasing chemically sensitive low k films without the complication of a permanent hardmask stack, yielding a single layer free-standing micromechanical beam with minimal chemical modifications from processing.

The method of the present invention provides (1) minimal alteration of the low k film during processing, (2) no added complexity in analysis of low k films by having multiple layers present on the released structure (Mechanical properties of free-standing structures are very sensitive to variations in film thickness and stiffness and such properties can be greatly modified by the additions of different layers. A clean simple structure is desired not to skew measurements), and (3) no conformability issues in thin low k films and no limitation in etch depth below the released structure. For structures to follow ideal conditions, conformal structures should be avoided, in addition to be able to deflect, or to allow structures to deflect downwards, there must be no fixed boundary underneath the free-standing structure.

The present invention achieves the above by using a low temperature (preferably on the order of about 25° C. to 200° C.) $XeF_2$ release process which is very selective to low k materials and when combined with a dual release layer and protective layer technique, a low k free-standing device (or structure) can be formed using a single release step.

In broad terms, the method of the present invention comprises the steps of:

providing a structure including a Si-containing substrate having in-laid etch stop layers located therein;

forming a chemically sensitive low k film and a protective hardmask having a pattern atop said structure;

transferring said pattern to said chemically sensitive low k film to provide an opening that exposes a portion of said Si-containing substrate; and etching said exposed portion of said Si-containing substrate through said opening to provide a cavity in said Si-containing substrate in which a free-standing low k film structure is formed, while removing said hardmask, said etching comprises a $XeF_2$ etch gas.

DETAILED DESCRIPTION OF THE INVENTION

The present invention, which provides a method for obtaining a free-standing micro structure, will now be described in greater detail by referring to the drawings that accompany the present application. It is noted that the drawings of the present invention are provided for illustrative purposes and thus they are not drawn to scale.

FIGS. 1–8 describe the inventive process flow and illustrate the material stack used in the creation of a low k film to be released using a combined sacrificial and protective release layer method. The trench dielectric formed into the Si-containing substrate will act as a selective etch-stop for the release process within the Si-containing substrate and will define the area of the released low k film. Alternatively, a Si-containing trench within an insulating region such as a buried oxide region will define the area of the released low k film. In accordance with the present invention, the Si-containing substrate, or sacrificial trench will be isotropically etched using $XeF_2$ gas chemistry.

Figure 1A:
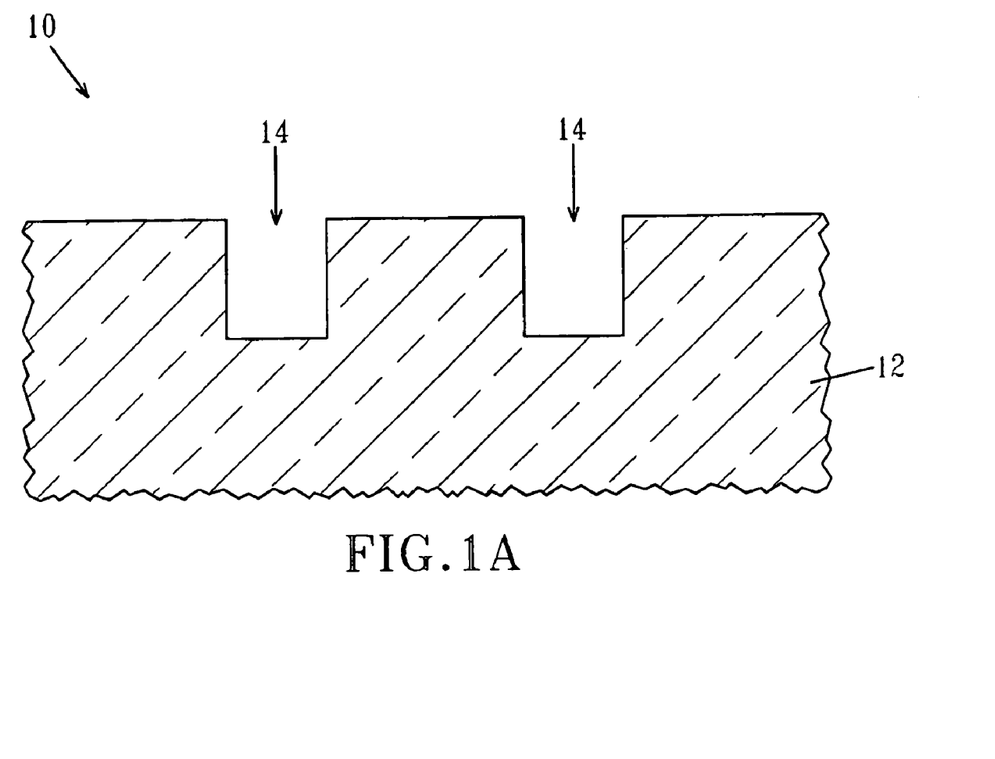
FIG. 1A is a pictorial representation (through a cross sectional view) illustrating a Si-containing substrate after trenches have been formed therein.
Figure 1B:
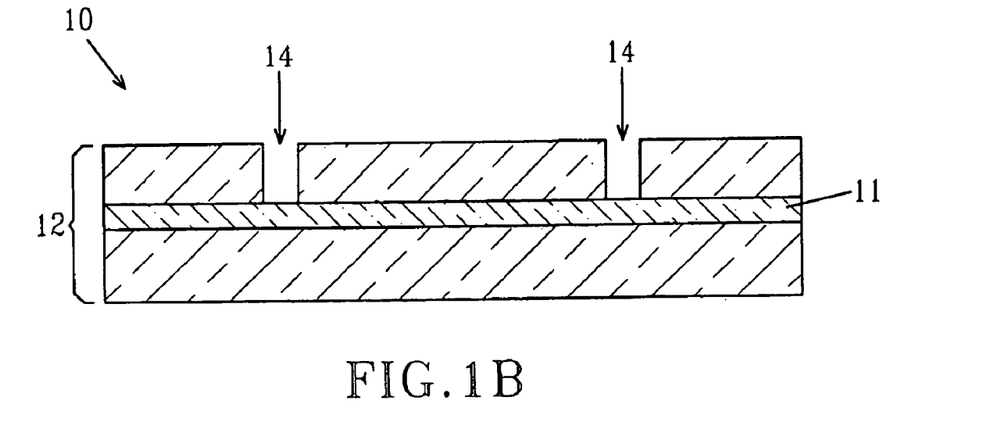
FIG. 1B is a pictorial representation (through a cross sectional view) illustrating a SOI substrate after trenches have been formed therein stopping on the lower oxide layer.

Reference is first made to FIG. 1A which shows a structure 10 that includes a Si-containing substrate 12 having at least one trench opening 14 formed therein. The term "Si-containing substrate" is used in the present invention to denote a semiconducting material that includes Si. Illustrative, the Si-containing substrate 12 may be comprised of Si, SiGe, SiGeC, SiC, silicon-on-insulators (SOIs) as shown in FIG. 1B, SiGe-on-insulators (SGOIs) and other like Si-containing material. The Si-containing substrate 12 can be doped or undoped. The Si-containing substrate 12 may be strained or unstrained and it may include any crystallographic orientation including the major or minor Miller indices. In some embodiments, the Si-containing substrate 12 may be a hybrid oriented substrate containing at least two planar surfaces of different crystallographic orientation. In FIG. 1B, reference numerals 12 and 14 have the same meaning as defined above, while reference numeral 11 denotes a buried insulating layer. The buried insulating layer can be an oxide, nitride, oxynitride or any combination thereof, with buried oxides being highly preferred.

The trench openings 14 are formed into the Si-containing substrate 12 utilizing a conventional process that includes photolithography and etching. The photolithographic process includes applying at least a photoresist (not shown) to the surface of the Si-containing substrate 12, exposing the photoresist to a desired pattern of radiation and developing the exposed photoresist using a conventional resist developer. The etch process used in forming the trench openings 14 includes a dry etch process such as reactive ion etching (RIE), plasma etching, ion beam etching and laser ablation. In some embodiments, a wet chemical etch can be used to provide the trench openings 14. After forming the trench openings 14 into the Si-containing substrate 12, the patterned photoresist is typically removed utilizing a conventional resist stripping process.

Figure 2:
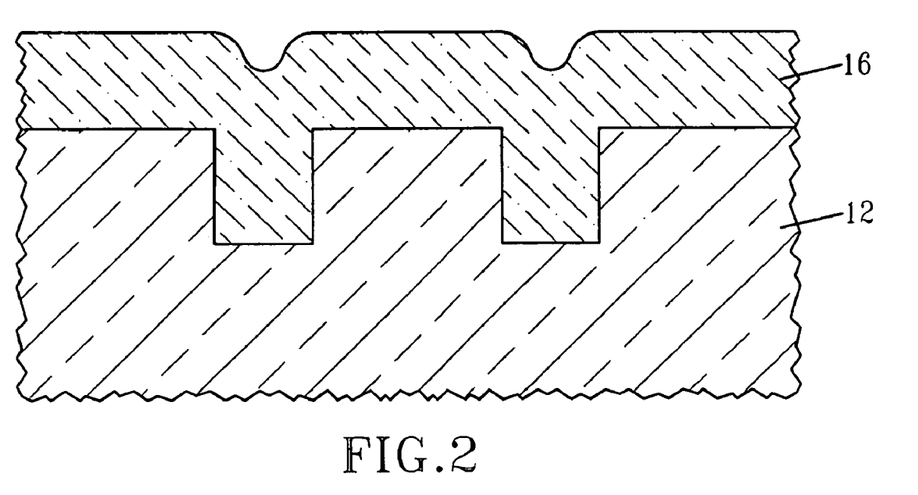
FIG. 2 is a pictorial representation (through a cross sectional view) illustrating the structure of FIG. 1A after forming a trench dielectric on the surface of the Si-containing substrate and within the trench openings.

Next, and as shown in FIG. 2, a trench dielectric 16 is formed on the structure shown in FIG. 1A including atop the Si-containing substrate 12 as well as within the trench openings 14. In a similar manner, the trench openings 14 within the SOI substrate 12 can be filled with a trench dielectric 16; this embodiment is not shown in the drawings. The trench dielectric 16 includes any insulating material including, for example, oxides, nitrides or oxynitrides. In a preferred embodiment, the trench dielectric 16 is an oxide. The trench dielectric 16 is formed utilizing a conventional deposition process including, for example, chemical vapor deposition (CVD), plasma enhanced chemical vapor deposition (PECVD), evaporation, chemical solution deposition and other like conformal deposition processes.

The thickness of the trench dielectric 16 deposited is not critical to the present invention and may vary depending upon the desired depth of the trench openings 14. Typically, the trench dielectric 16 has a thickness from about 100 to about 5000 nm. When a substrate including a buried insulating layer is used, the etch depth is predefined by thickness of top Si layer.

In some embodiments, the trench openings 14 can be lined with a diffusion barrier material such as, for example TiN, prior to deposition of the trench dielectric 16. Also, after deposition of the trench dielectric 16, the trench dielectric 16 may be subjected to a densificiation process that hardness, i.e., densifies the trench dielectric 16. When densification occurs, it typically is performed after that trench dielectric 16 has been planarized.

Figure 3A:
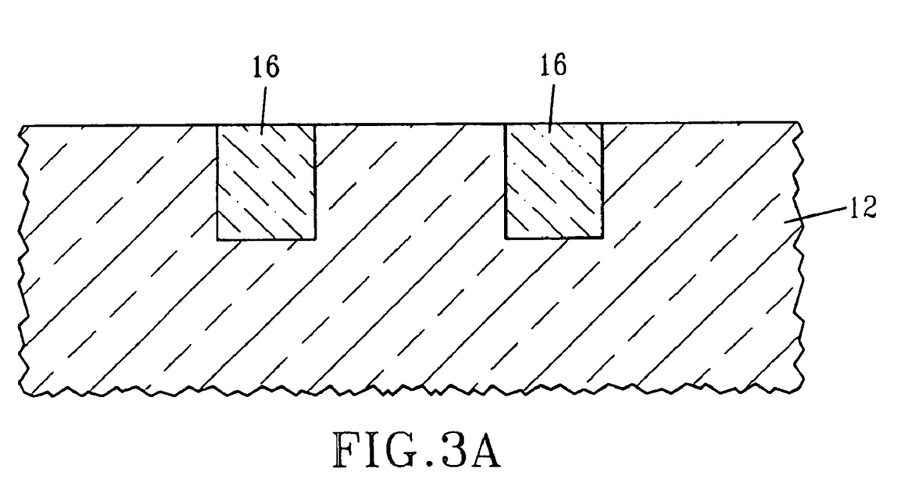
FIG. 3A is a pictorial representation (through a cross sectional view) illustrating the structure of FIG. 2 after subjecting the same to a planarization process.
Figure 3B:
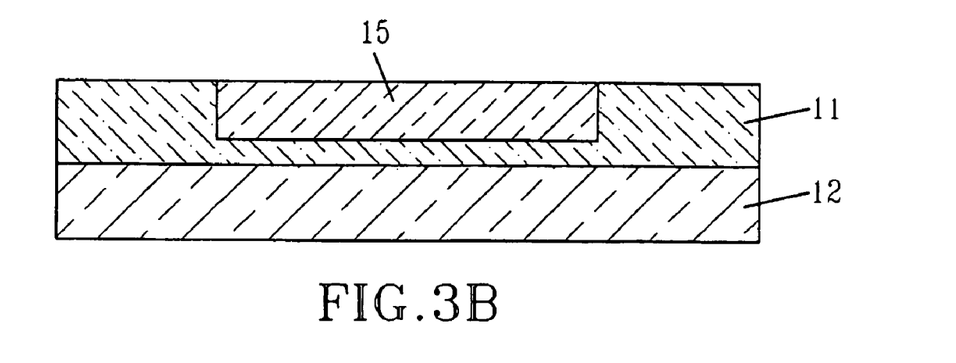
FIG. 3B is a pictorial representation (through a cross sectional view) illustrating an alternative to the structure of FIG. 3A in which a sacrificial Si layer is inlaid in an oxide layer after subjected to a planarization process.

FIG. 3A shows the structure after the trench dielectric 16 has been planarized such that an upper surface thereof is coplanar with an upper surface of the Si-containing substrate 12. Alternatively, a trench Si-sacrificial layer 15 is inlaid in the insulating layer 11, preferably an oxide, using techniques well known in the art. Such a structure is shown in FIG. 3B. Specifically, FIG. 3B shows a planarized structure with trench Si layer 15 coplanar with an upper surface of insulating layer 11. Any conventional planarization process including, for example, chemical mechanical polishing (CMP) or grinding can be used. The in-laid trench dielectric 15 shown in FIG. 3B will later act as etch stops for the isotropically etching of the Si-containing substrate 12 to form and define a cavity below the free-standing structure. After additional processing as defined herein below, the structure shown in FIG. 3B will yield a free-standing structure following isotropically etching of the inlaid trench Si 15.

After planarization, a material layer stack comprising at least a low k dielectric film 18, either a single or dual layer protective hardmask 20, and a photoresist 22 is formed on the structure shown in FIG. 3A (or alternatively FIG. 3B). The term "low k film" is used throughout the instant application to denote a dielectric material having a dielectric constant k, that is less than silicon dioxide. Typically, silicon dioxide has a dielectric constant, as measured in a vacuum, of about 4.0. Thus, the low k film 18 formed has a dielectric constant, as measured in a vacuum, of less than 4.0, preferably less than 3.7. The low k dielectric film 18 can be porous or non-porous, with non-porous materials being preferred. If a porous low k film is to be employed and is to be analyzed, the Si underneath the low k film might get attacked during release. Thus, the structure shown in FIG. 3B will typically be used to provide sufficient adhesion between free-standing low k film and substrate.

The low k film 18 can include any chemically-sensitive inorganic or organic dielectric whose dielectric constant is within the range mentioned above. Illustratively, the low k film 18 may include an organic silicate glass such as, for example, a carbon doped oxide comprising atoms of Si, C and O, polyarylene ethers such as SiLK® (sold by the Dow Chemical Co.), and Si-containing polymers including silsequioxanes and organosilanes.

The low k film 18 may be formed by a deposition process including, for example, CVD, PECVD, evaporation, chemical solution deposition, spin-on coating and other like deposition processes. The thickness of the low k dielectric film 18 may vary depending on the type of device to be formed, the type of low k material being deposited and the method that was used to form the same. Typically, the low k film 18 has a thickness from, but not limited to, 200 to about 5000 nm, with a thickness from about 1000 to about 3000 nm being more typical.

The protective hardmask 20 is formed atop a surface of the low k film 18 utilizing a conventional deposition process such as CVD, PECVD, evaporation, chemical solution deposition and other like deposition processes. The protective hardmask 20 may comprise Ta, TaN, Si, Mo, Ti, TiN, TiW, W or any combination thereof, including multilayers known to etch in $XeF_2$ chemistry. The protective hardmask 20 typically has a thickness from about 20 to about 1000 nm, with a thickness from about 300 to about 500 nm being more typical.

Figure 5A:
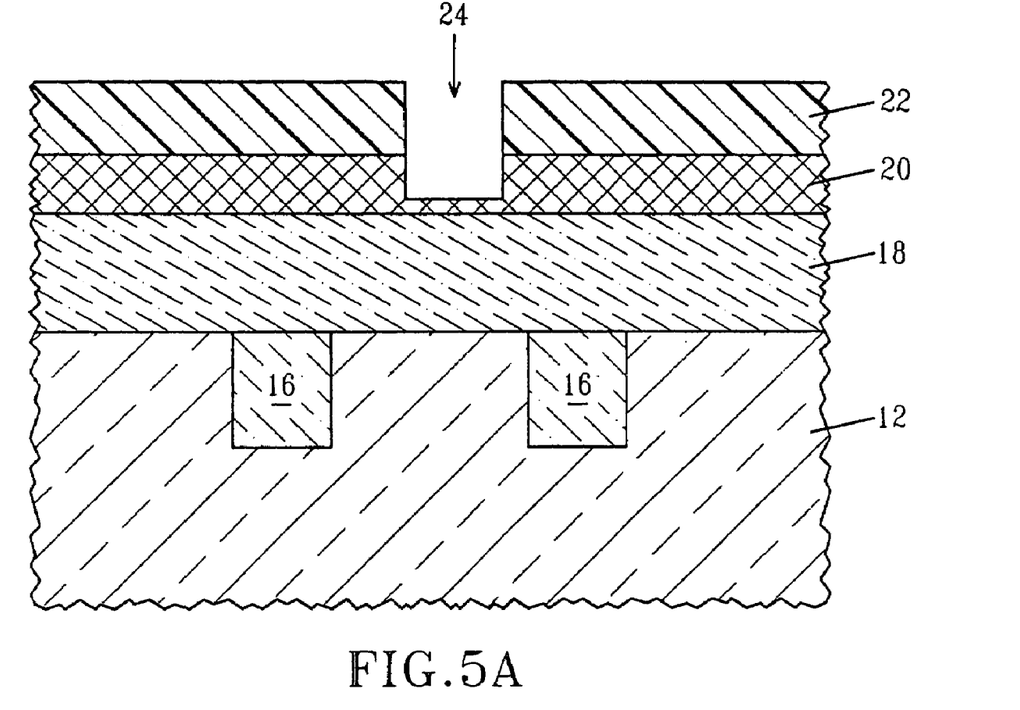
FIG. 5A is a pictorial representation (through a cross sectional view) illustrating the structure of FIG. 4 after the pattern has been partially transferred from the patterned photoresist to the underlying protective hardmask.
Figure 5B:
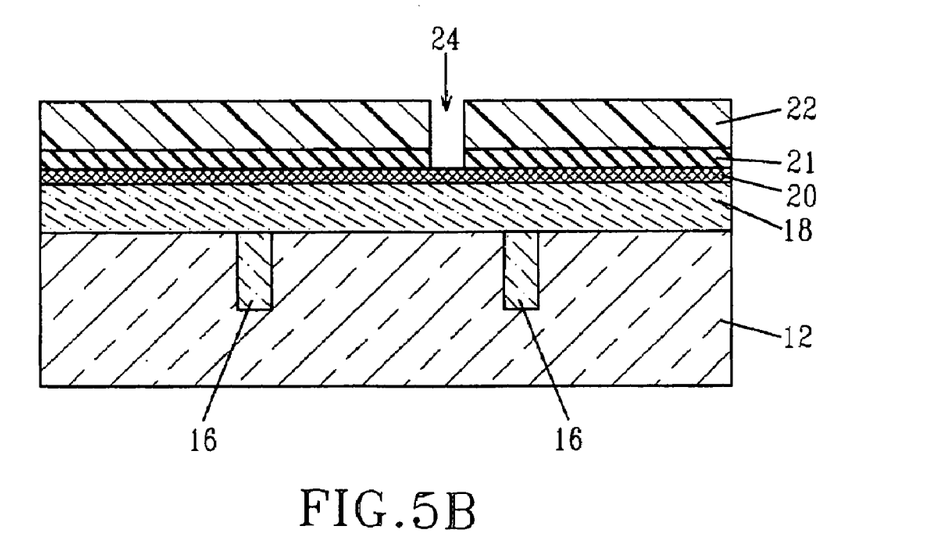
FIG. 5B is a pictorial representation (through a cross sectional view) illustrating the structure of FIG. 4 with an additional patterned hardmask deposited on top of the protective hardmask.

Alternatively, if a dual hard mask approach is to be used as shown in FIG. 5B, the second hardmask 21 may comprise an oxide, nitride or oxynitride including multilayer thereof.

The photoresist 22 is applied to an exposed surface of the hardmask 20 utilizing a conventional deposition process, including, for example, spin-on coating. The photoresist 22 comprises an organic material that is capable of being patterned. The photoresist 22 can be a negative-tone resist material or a positive tone resist material. The thickness of the applied photoresist 22 is not critical to the present invention.

Figure 4:
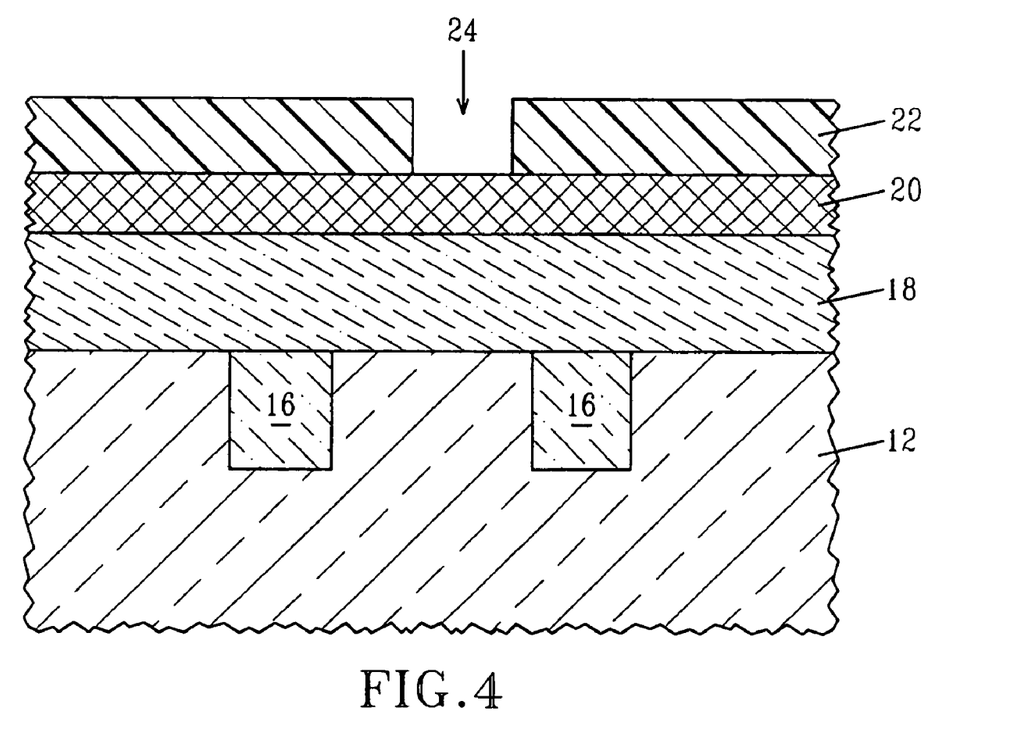
FIG. 4 is a pictorial representation (though a cross sectional view) illustrating the structure of FIG. 3A after forming a low k dielectric film, a protective hardmask and a patterned photoresist.

After forming the material stack described above, the photoresist 22 is patterned, such as shown in FIG. 4, utilizing photolithography. The patterned photoresist 22 has at least one opening 24 formed therein.

The pattern provided to the photoresist 22 is then partially transferred to the underlying protective hardmask 20 utilizing an etching process that selectively removes exposed portions of the hardmask 20. A timed etching process such as RIE, or similar is typically used to partially transfer the pattern to the hardmask 20. The resultant structure is shown, for example, in FIG. 5A.

For a dual hardmask structure shown in FIG. 5B, the pattern provided by the photoresist 22 is completely transferred to the underlying protective top hardmask 21 utilizing an etching process that selectively removes exposed portions of the hardmask 21. After the pattern has been transferred to the top hardmask 21, the pattern is then transferred into the lower hardmask 20 by etching.

Figure 6:
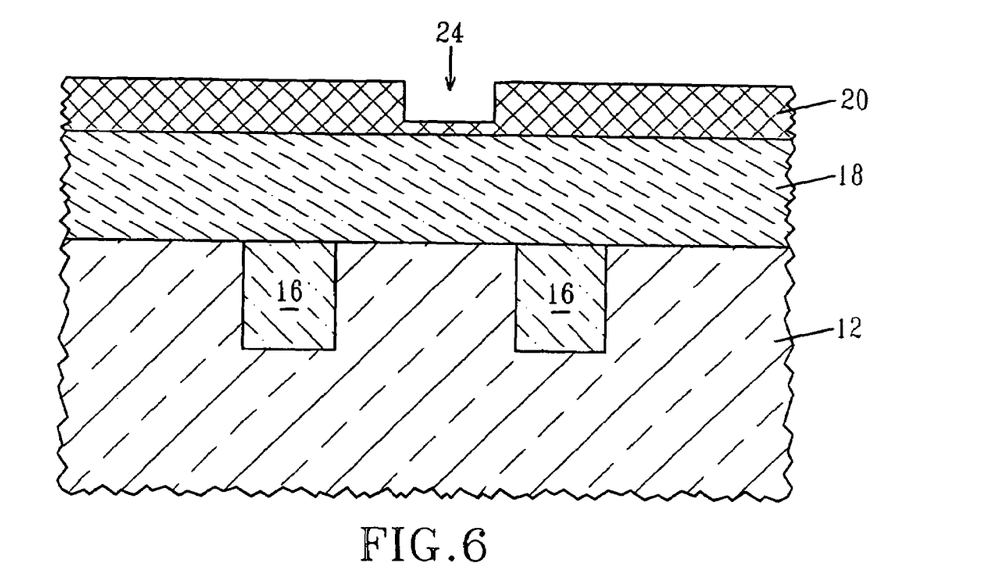
FIG. 6 is a pictorial representation (through a cross sectional view) illustrating the structure of FIG. 5A after the patterned photoresist has been removed.

Next, and as shown in FIG. 6, the patterned photoresist 22 is removed from the structure utilizing a conventional resist stripping process, which might, or might not affect hardmask 20 or 21, but will not compromise low k film 18 which remains protected by hardmask 20.

Figure 7A:
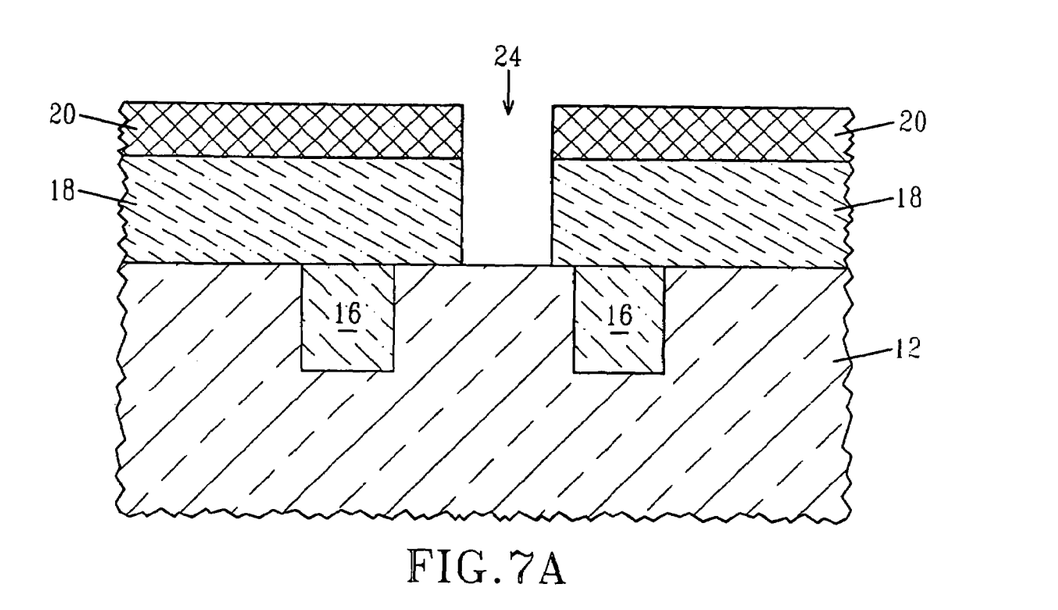
FIG. 7A is a pictorial representation (through a cross sectional view) illustrating the structure of FIG. 6 after transferring the pattern from the protective hardmask to the low k film and partial removal of the protective hardmask.
Figure 7B:
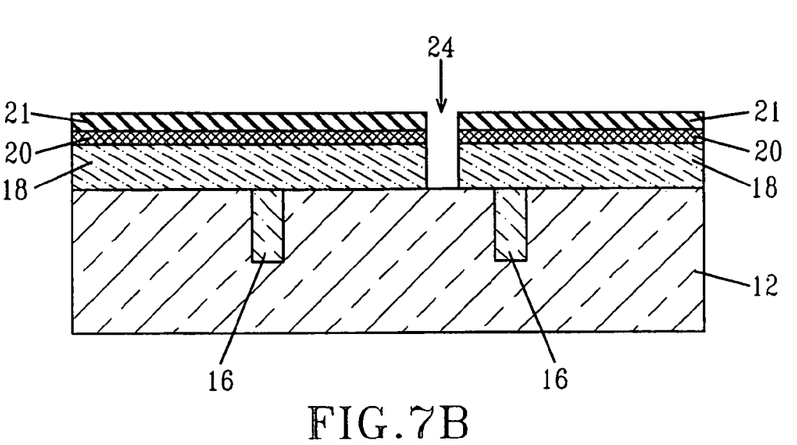
FIG. 7B is a pictorial representation (through a cross sectional view) illustrating the structure of FIG. 5B after the patterned photoresist has been removed and the pattern from the top protective hardmask has been transferred to the low k film.

After the patterned photoresist 22 has been removed from the structure, the pattern that was partially formed in the hardmask 20, or completely transferred in hardmask 21 by the steps mentioned above is then transferred to the low k film 18 so as to expose a surface of Si-containing substrate 12. This step of the present invention utilizes an etching process such as RIE that is suitable for partially thinning the hardmask 20, as well as removing the exposed portion of the low k film 18. In accordance with the present invention, the hardmask 20 prevents extensive damage to the chemically sensitive low k film 18. The resultant structure is shown in FIG. 7A. It is noted that in the resultant structure a portion of the hardmask 20 remains on the surface of the chemically sensitive low k film 18. For the dual hardmask structure illustrated in FIG. 7B, the patterned hardmask 21 will be in place while patterning of low k film 18 as shown in FIG. 7B, and subsequently removed. During the removal process of hardmask 21, the lower hardmask 20 will protect the low k material from extensive damage.

Figure 8A:
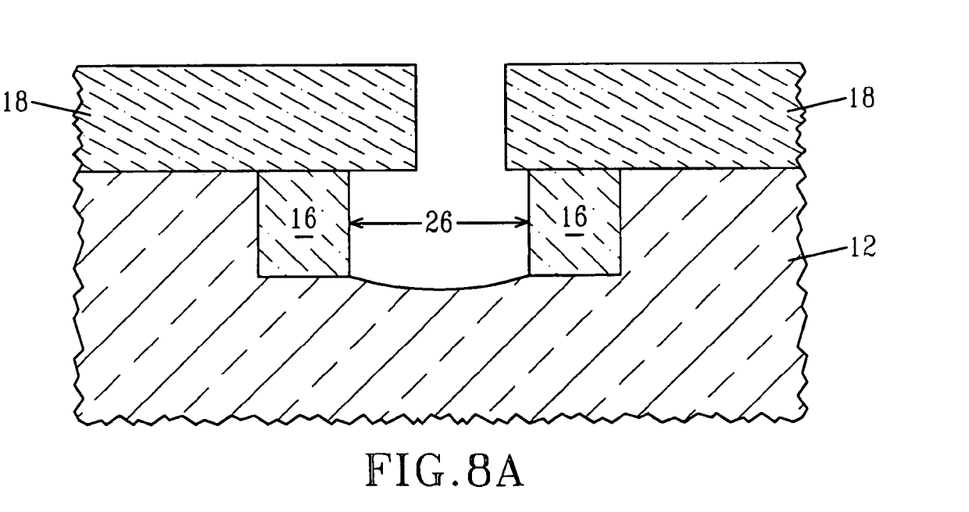
FIG. 8A is a pictorial representation (through a cross sectional view) illustrating the structure of FIG. 7A after subjecting the same to the inventive etching process which will both etch the sacrificial layer and the protective hardmask at same time using the same.
Figure 8B:
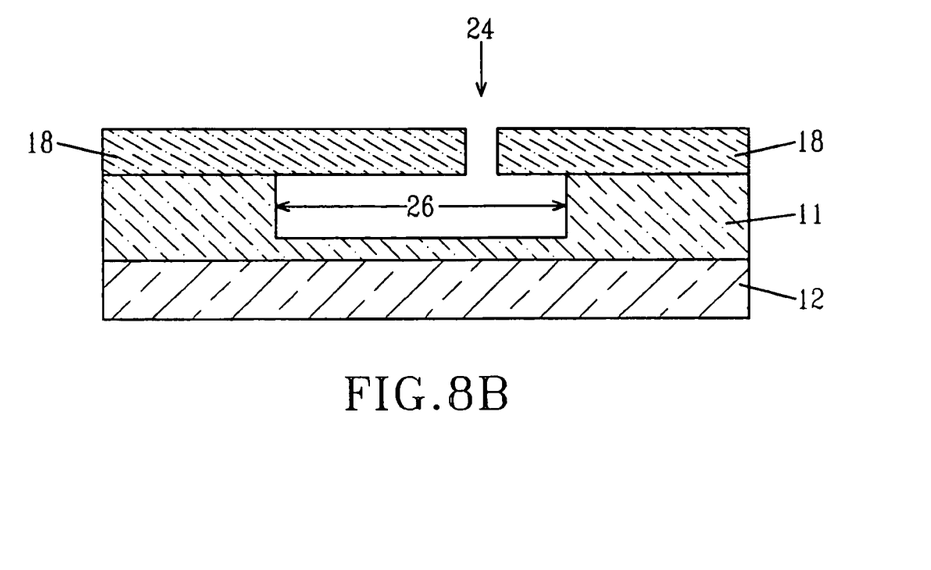
FIG. 8B is a pictorial representation (through a cross sectional view) illustrating an alternative to FIG. 8A using an inlaid sacrificial layer and subjecting the same to the inventive etching process, which will both etch the sacrificial layer and the protective hardmask at same time.

FIG. 8A shows the structure after cavity 26 has been formed into the Si-containing substrate 12 though opening 24. As shown, a free-standing structure, i.e., portions of the low k film 18 remain. The structure including the cavity 26 and the free-standing structure is formed utilizing an isotropic etching process that selectively removes the exposed portion of the Si-containing substrate 12 and protective hardmask 20. Hence, this etching step of the present invention removes the hardmask 20 and forms the cavity in a single process step. FIG. 8B shows the same end result using an inlaid sacrificial layer 15 which when removed defines the cavity 26.

As indicated above, the structure shown in FIG. 8A (or 8B) is formed utilizing an isotropic etching step that selective removes silicon and some selected metals used as a hard mask. In accordance with the present invention, the isotropic etching step used to create the cavity 26, while removing the protective hardmask 20 includes $XeF_2$ gas chemistry. Any suitable $XeF_2$ process might be used for this process. Typically, the partial pressure of $XeF_2$ employed is from about 0 to about 20 mTorr. An example of a $XeF_2$ process is the use of a dual chamber process in which the first expansion chamber is at a low pressure (0.5–3 Torr) and the second chamber is at a lower pressure (0–20 mTorr).

A solid source of $XeF_2$ is then exposed to the first chamber which is kept at a lower pressure than the vapor pressure of $XeF_2$. At room temperature, the vapor pressure of $XeF_2$ is 3.9 Torr. In the first chamber, sublimed $XeF_2$ and $N_2$ gas is collected before entering the process (second) chamber where the wafer/sample will be exposed to the $XeF_2$ gas. The exposure time is typically set, but not limited to anywhere between 1 and 100 seconds depending on desired etch specifications. When the etch time is up, both the remaining $XeF_2$ gas and $N_2$ carrier gas is pumped out.

This process is set to repeat as many times as needed to obtain desired etch result, and both chambers might be filled with $N_2$ gas to aid in removal of $XeF_2$ from the structure. Other gases may be diluted to the $XeF_2$ etch process to either improve selectivity or to clean the etched sample. Additionally the temperature of the substrate may be controlled from anywhere between 0 and 400° C., with a temperature from about 25° to 200° C. being highly preferred.

Figure 9:
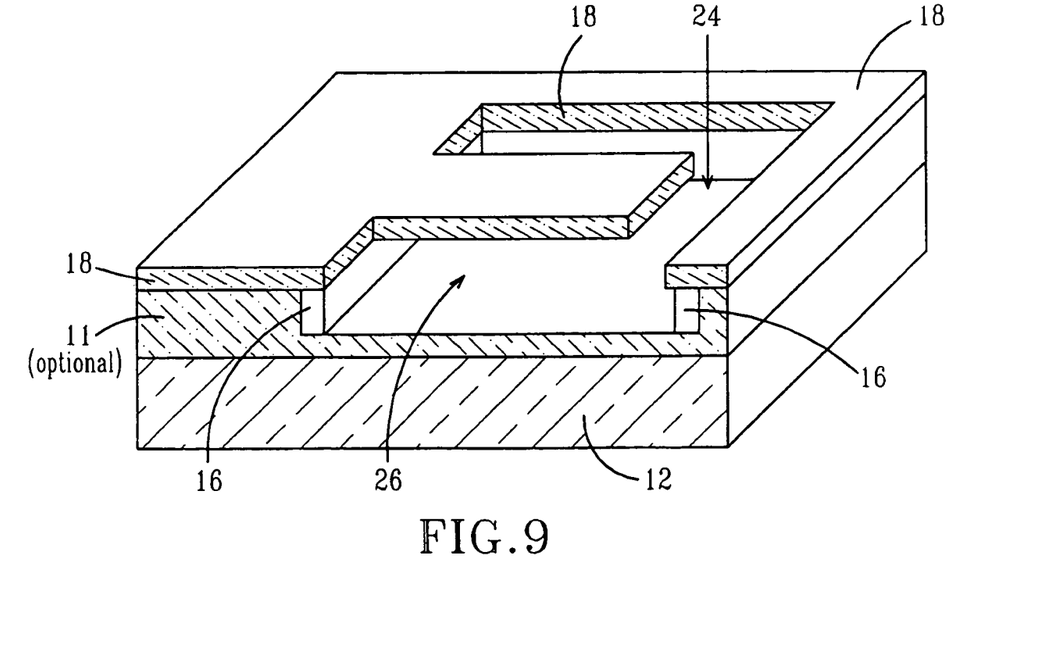
FIG. 9 is a pictorial representation (through a quasi three-dimensional view) illustrating the structure shown in FIG. 8.

FIG. 9 is a pictorial representation (through a quasi three-dimensional view) illustrating the structure shown in FIG. 8. Note that the insulating layer 11 is optional.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A method of fabricating a free-standing micro structure comprising:
    providing a structure including a Si-containing substrate having in-laid etch stop layers located therein;
    forming a chemically sensitive low k film and a protective hardmask having a pattern atop said structure;
    transferring said pattern to said chemically sensitive low k film to provide an opening that exposes a portion of said Si-containing substrate; and
    etching said exposed portion of said Si-containing substrate through said opening to provide a cavity in said Si-containing substrate in which a free-standing low k film structure is formed, while removing said hardmask, said etching comprises a $XeF_2$ etch gas.

2. The method of claim 1 wherein said Si-containing substrate comprises Si, SiGe, SiGeC, SiC, a silicon-on-insulator or a SiGe-on-insulator.

3. The method of claim 1 wherein said in-laid etch stop layers comprise a trench dielectric material.

4. The method of claim 1 wherein said in-laid etch stop layers comprise a trench of Si material within a buried insulating layer.

5. The method of claim 1 wherein said in-laid etch stop layers comprise a trench of TaN, W, TiN or Mo metal.

6. The method of claim 1 wherein said in-laid etch stop layers are formed by lithography, etching, and trench fill.

7. The method of claim 1 wherein said chemically sensitive low k film has a dielectric constant less than 3.7.

8. The method of claim 1 wherein said chemically sensitive low k film is porous or non-porous.

9. The method of claim 1 wherein said chemically sensitive low k film is an organic or inorganic dielectric.

10. The method of claim 1 wherein said chemically sensitive low k film comprises an organic silicate glass, a polyarylene ether or a Si-containing polymer.

11. The method of claim 1 wherein said protective hardmask includes one of Ta, TaN, Si, Mo, Ti, TiN or W.

12. The method of claim 1 wherein said etching is isotropic.

13. The method of claim 1 wherein said etching is performed at a temperature from about 0° to about 400° C.

14. The method of claim 1 wherein said etching is performed using a partial pressure of $XeF_2$ from about 0 to about 20 mTorr.

15. A method for fabricating a micro structure comprising
    performing a gas etching process using $XeF_2$ as an etchant on a structure that includes a patterned hardmask, a patterned chemically sensitive low k film which exposes a portion of an underlying Si-containing substrate, whereby said gas etching process removes said exposed portion of the Si-containing substrate providing a free-standing low k film structure atop the Si-containing substrate, while also removing the patterned hardmask.

16. The method of claim 15 wherein said Si-containing substrate comprises Si, SiGe, SiGeC, SiC, a silicon-on-insulator or a SiGe-on-insulator.

17. The method of claim 15 wherein said Si-containing substrate includes in-laid etch stop layers that comprise a trench dielectric material.

18. The method of claim 17 wherein said in-laid etch stop layers are formed by lithography, etching, and trench fill and planarization.

19. The method of claim 15 wherein said chemically sensitive low k film has a dielectric constant less than 3.7.

20. The method of claim 15 wherein said chemically sensitive low k film is porous or non-porous.

21. The method of claim 15 wherein said chemically sensitive low k film is an organic or inorganic dielectric.

22. The method of claim 15 wherein said chemically sensitive low k film comprises an organic silicate glass, a polyarylene ether or a Si-containing polymer.

23. The method of claim 15 wherein said patterned hardmask includes one of Ta, TaN, Si, Mo, Ti, TiN or W or compounds thereof.

24. The method of claim 15 wherein said gas etching process is isotropic.

25. The method of claim 15 wherein said gas etching process is performed at a temperature from about 0° to about 400° C.

26. The method of claim 15 wherein said gas etching process is performed using a partial pressure of $XeF_2$ from about 0 to about 20 mTorr.

* * * * *